United States Patent [19]

Deetman

[11] 4,386,224

[45] May 31, 1983

[54] COLOR STABILIZATION OF MONOALKYL PHENOLS

[75] Inventor: Gerbrand Deetman, Hazelwood, Mo.

[73] Assignee: Monsanto Company, St. Louis, Mo.

[21] Appl. No.: 297,683

[22] Filed: Aug. 31, 1981

[51] Int. Cl.$^3$ ............................................. C07C 37/88
[52] U.S. Cl. .................................... 568/703; 568/780; 568/749
[58] Field of Search .................... 568/703, 749, 780

[56] References Cited

U.S. PATENT DOCUMENTS

| | | | |
|---|---|---|---|
| Re. 24,834 | 6/1960 | Menn et al. ........................ | 568/703 |
| 2,672,485 | 3/1954 | Martinez et al. ................... | 260/624 |
| 2,727,928 | 12/1955 | Martinez et al. ................... | 260/624 |
| 2,752,398 | 6/1956 | Riley ................................. | 260/624 |
| 2,877,273 | 3/1959 | Enos, Jr. ............................ | 260/624 |
| 2,886,601 | 5/1959 | Clough .............................. | 568/703 |
| 3,168,578 | 2/1965 | Ginos et al. ........................ | 260/624 |
| 3,553,272 | 1/1971 | Riley ................................. | 260/264 |
| 3,629,339 | 12/1971 | Schlichting et al. ............. | 260/261 A |
| 4,054,611 | 10/1977 | Mimaki et al. ..................... | 568/703 |

*Primary Examiner*—Werren B. Lone
*Attorney, Agent, or Firm*—Jon H. Beusen; William H. Duffey; Robert C. Griesbauer

[57] ABSTRACT

A method for stabilizing color, inhibiting color development, and reducing color of monoalkyl phenols by incorporation of N,N-diethylhydroxylamine, preferably from about 5 parts per million to about 50 parts per million. Also a color stabilized monoalkyl phenol composition comprising a monoalkyl phenol and a color stabilizing amount of N,N-diethylhydroxylamine.

12 Claims, No Drawings

COLOR STABILIZATION OF MONOALKYL PHENOLS

BACKGROUND OF THE INVENTION

1. Field of the Invention

This invention relates to the color stabilization of monoalkyl phenols, which frequently discolor with age. More specifically, this invention relates to improving the color stability of monoalkyl phenols and reducing color already formed by the addition of an additive.

2. Background Discussion

Monoalkyl phenols are generally produced by reacting phenol with an olefin in the presence of an acidic alkylation catalyst. The product should be only lightly colored, but color frequently develops with age. Sometimes color development is rapid. Color development substantially reduces the commercial value of monoalkyl phenols, because many uses require material that is only lightly colored. Neither the identity of the colored species nor the mechanism of their production are exactly known. However, the speed and degree of the color development are affected by a number of factors, including: the presence of metallic impurities, of residual catalyst, and of reaction byproducts; exposure of the product to oxygen, to sunlight, to HCl, and to steel containers; and the temperature at which storage occurs.

A number of additives are known that act to inhibit color formation in alkyl phenols, including: polybasic carboxylic acids (U.S. Pat. No. 2,672,485); phosphoric acid (U.S. Pat. No. 2,752,398); dicarboxylic acid substituted abietylamines and their salts (U.S. Pat. No. 2,877,273); hypophosphorous acid and its salts used either as an additive to the product (U.S. Pat. No. 2,727,928) or as an additive to the phenol starting material (U.S. Pat. No. 3,168,578); organic phosphites (U.S. Pat. No. 3,553,272); and various arsenic compounds (U.S. Pat. No. 3,629,339). Although each of these color stabilizers is effective to some extent, with at least some alkyl phenols, none is effective under all circumstances.

The lower limit of effective concentrations disclosed for the above listed color inhibitors ranges from 0.001% by weight for phosphoric acid and the arsenic compounds to 0.15% for hypophosphorous acid. The upper limit of concentrations claimed for the above listed color inhibitors ranges from 0.1% for phosphoric acid to 5% for abietylamine derivatives.

An advantage of this invention is stabilization of color and inhibition of color development of monoalkyl phenols. A further advantage of this invention is reduction of color of monoalkyl phenols in which color development has taken place. It is still further an advantage of this invention that adequate color stability, inhibition, and reduction are accomplished with an additive used at lower concentrations than prior art additives. Further advantages will become apparent from the discussion and examples.

SUMMARY OF THE INVENTION

One embodiment of this invention is a method for stabilizing color, inhibiting color formation, and reducing color already formed in monoalkyl phenols by addition of N,N-diethylhydroxylamine, preferably in amounts ranging from about 5 parts per million (0.0005%) to about 50 parts per million (0.005%) by weight of the alkyl phenol. Another embodiment of this invention is a monoalkyl phenol containing a color stabilizing amount of N,N-diethylhydroxylamine.

DESCRIPTION OF THE PREFERRED EMBODIMENTS

N,N-diethylhydroxylamine can be produced by oxidation of triethylamine with hydrogen peroxide or a percarboxylic acid to form triethylamine oxide, which decomposes upon strong heating to form N,N-diethylhydroxylamine and ethylene, or by oxidation of diethyl amine with hydrogen peroxide or a percarboxylic acid, to form N,N-diethylhydroxylamine. N,N-diethylhydroxylamine is used in photographic developers, as an oxygen scavenger in high pressure boiler water systems, and as a radical chain stopping reactant in polymerization reactions.

N,N-diethylhydroxylamine has been shown to be surprisingly effective in stabilizing color and inhibiting color formation in monoalkyl phenols and in reducing discoloration that has occurred, even though present in very low concentrations.

The monoalkyl phenols used in the examples were prepared by alkylation of phenol with appropriate olefins in the presence of a sulfonated polystyrene alkylation catalyst. Color was determined according to the American Public Health Association standard color test, which is well known to those skilled in the art as the APHA color test. A description of the APHA color test can be found in volume 2, part 13, on page 2425 of the 6th edition of "Standard Methods of Chemical Analysis", F. J. Welcher, editor. Color is expressed numerically, with a higher number indicating a darker color.

The following examples are used for illustrative purposes only and are not to be construed in any limiting sense. Percentages and parts are by weight unless otherwise specified.

EXAMPLE 1

A monoalkyl phenol was prepared by alkylating phenol with a mixture of about 90% nonene, and lesser amounts of $C_8$, $C_{10}$, and $C_{11}$ olefins. This product is commonly known as nonylphenol. A common manufacturing specification of nonyphenol is APHA color of 60.

Sample 1 was taken directly from the line leading from the production reactor and was left untreated as a standard.

Sample 2 was taken at the same time as Sample 1, but was treated with about 20 parts per million of N,N-diethylhydroxylamine.

Sample 3 was taken from the same production run, but was taken one day later from a steel storage tank that had been maintained at 60° C.

Sample 4 was taken on the same day as Sample 3 and from the same storage tank but after about 20 parts per million of N,N-diethylhydroxylamine had been incorporated into the contents of the tank.

Initial APHA color of the nonylphenol immediately after production was determined to be 20.

Each sample was placed in a 5 gallon metal can for shipment to the laboratory. Shipment occurred at ambient temperatures. Upon arrival at the laboratory, 17 days after production, APHA color was again determined. These results are shown in the second column of Table I. Samples 3 and 4 were stored at room temperature, and APHA color was again determined 50 days after production. These results are shown in the third column of Table I.

Upon arrival at the laboratory, 17 days after production, a test to determine the effects of prolonged storage at 60° C. was begun. A portion of each Sample was placed in a glass container and heated to 60° C. An additional portion of Sample 4 was placed in a glass container along with a steel coupon and was also heated to 60° C. This additional portion is Sample 5. APHA color of all five samples was determined after 7 weeks at 60° C. (a total of 66 days after production). These results are shown in the fourth column of Table I.

TABLE I

| | APHA COLOR OF NONYLPHENOL At Ambient Temperatures | | |
|---|---|---|---|
| Sample No. | 17 days after Production | 50 days after Production | After 7 wks.* at 60° C. |
| 1 | 140 | — | 45 |
| 2 | 15 | — | 25 |
| 3 | 325 | 500 | 110 |
| 4 | 35 | 35 | 45 |
| 5 | — | — | 110 |

*7 weeks at 60° C. was after 17 days at ambient temperature.

Comparison of the color of Sample 2 with Sample 1 and the color of Sample 4 with Sample 3 shows that addition of N,N-diethylhydroxylamine markedly reduces development.

It is known to those skilled in the art that heating of nonylphenol which had discolored will reduce the amount of color. This phenomenon is demonstrated by the APHA color data taken after 7 weeks of storage at 60° C. However, even in these Samples, the presence of N,N-diethylhydroxylamine resulted in a significantly lighter color.

EXAMPLE 2

Nonylphenol was prepared in a manner similar to that used in Example 1. After storage at room temperature for 72 days, APHA color was determined to be 90. N,N-diethylhydroxylamine (DEH) was added in various concentrations, and the mixtures were maintained at 60° C. for 21 days. After heating and addition of N,N-diethylhydroxylamine color was determined initially and at intervals thereafter. The results were summarized in Table II.

TABLE II

| | APHA COLOR OF NONYLPHENOL | | | | | | |
|---|---|---|---|---|---|---|---|
| | | Days at 60° C. | | | | | |
| [DEH], ppm | Initial | 4 | 7 | 11 | 14 | 18 | 21 |
| 5 | 40 | 55 | 65 | 75 | 75 | 112 | 112 |
| 10 | 40 | 40 | 48 | 65 | 65 | 85 | 85 |
| 25 | 40 | 55 | 55 | 55 | 65 | 85 | 85 |
| 50 | 40 | 65 | 65 | 55 | 65 | 85 | 85 |
| 100 | 52 | 95 | 95 | 85 | 55 | 55 | 55 |

Although the N,N-diethylhydroxylamine was effective at all concentrations tested, the preferred concentration was determined to be in the range of about 5 to about 50 parts per million, or more particularly about 20 parts per million. Above about 50 parts per million, the odor of the N,N-diethylhydroxylamine becomes noticeable.

EXAMPLE 3

A monoalkyl phenol was prepared by alkylating phenol in a manner similar to Example 1, with a mixture of olefins consisting of about 5% $C_{10}$, about 20% $C_{11}$, about 60% $C_{12}$, about 10% $C_{13}$, and minor amounts of higher olefins and impurities, which results in an average carbon number of the olefins of about 11.8. This product is commonly known and sold as dodecylphenol. Three samples of dodecylphenol were prepared for storage tests in glass containers. Twenty parts per million of N,N-diethylhydroxylamine was added to one sample. The DEH sample and one standard were held at 60° C. while the other standard was stored at 25° C. APHA color was determined at intervals. The results are tabulated in Table III.

TABLE III

| | APHA COLOR OF DODECYLPHENOL | | |
|---|---|---|---|
| Number of Days | 60° C. | | 25° C. |
| | DEH Sample | Standard | Standard |
| 0 | 65 | 65 | 65 |
| 3 | 45 | 65 | 65 |
| 14 | 65 | 110 | — |
| 23 | 75 | 120 | 65 |
| 31 | 110 | 187 | 65 |

Although dodecylphenol color formation differs from nonylphenol color formation in that the former is accelerated by raised temperatures while the latter is retarded by raised temperatures, the addition of N,N-diethylhydroxylamine also inhibited color formation in dodecylphenol.

In addition to the effects described above, addition of N,N-diethylhydroxylamine was observed to reduce color that had previously formed.

The previous Examples are intended as illustrative and are not meant in any way to limit the scope of this invention.

What is claimed is:

1. A composition, comprising a monoalkyl phenol with an alkyl group from $C_8$ to $C_{13}$ and a color stabilizing amount of N,N-diethylhydroxylamine.

2. The composition of claim 1 in which N,N-diethylhydroxylamine is present from about 5 to about 50 parts per million by weight of monoalkyl phenol.

3. The composition of claim 1 in which the monoalkyl phenol is nonylphenol.

4. The composition of claim 1 in which the monoalkyl phenol is dodecylphenol.

5. A method of inhibiting color development in a monoalkylphenol with an alkyl group from $C_8$ to $C_{13}$, which comprises incorporation of a color stabilizing amount of N,N-diethylhydroxylamine into the monoalkyl phenol.

6. The method of claim 5 in which the N,N-diethylhydroxylamine is added in an amount sufficient to comprise from about 5 to about 50 parts per million by weight of monoalkyl phenol.

7. The method of claim 5 in which the monoalkyl phenol is nonylphenol.

8. The method of claim 5 in which the monoalkyl phenol is dodecylphenol.

9. A method of reducing the color of a monoalkyl phenol with an alkyl group from $C_8$ to $C_{13}$ in which color development has occurred, which comprises incorporation of a color reducing amount of N,N-diethylhydroxylamine into the monoalkyl phenol.

10. The method of claim 9 in which the N,N-diethylhydroxylamine is incorporated in an amount sufficient to comprise from about 5 to about 50 parts per million by weight of monoalkyl phenol.

11. The method of claim 9 in which the monoalkyl phenol is nonylphenol.

12. The method of claim 9 in which the monoalkyl phenol is dodecylphenol.

* * * * *